(12) United States Patent
Rehm

(10) Patent No.: US 6,440,064 B1
(45) Date of Patent: Aug. 27, 2002

(54) APPARATUS FOR RETRACTING TISSUE DURING SURGICAL PROCEDURES

(75) Inventor: Walter Rehm, Tuttlingen (DE)

(73) Assignee: Max Hauser Süddeutsche Chirurgiemechanik GmbH, Tuttlingen (DE)

( * ) Notice: Subject to any disclaimer, the term of this patent is extended or adjusted under 35 U.S.C. 154(b) by 0 days.

(21) Appl. No.: 09/628,785

(22) Filed: Jul. 29, 2000

(30) Foreign Application Priority Data

Jul. 29, 1999 (DE) .......................................... 199 35 394

(51) Int. Cl.[7] .................................................. A61B 1/32
(52) U.S. Cl. ........................................ 600/232; 600/231
(58) Field of Search ................................ 600/213, 231, 600/232, 233, 227

(56) References Cited

U.S. PATENT DOCUMENTS

| | | | | |
|---|---|---|---|---|
| 1,613,141 A | * | 1/1927 | Stein | 600/232 |
| 2,450,194 A | * | 9/1948 | Glaser | 600/232 |
| 2,670,731 A | * | 3/1954 | Zoll et al. | |
| 4,865,019 A | * | 9/1989 | Phillips | 600/232 |
| 4,989,587 A | * | 2/1991 | Farley | 600/232 X |
| 5,052,373 A | * | 10/1991 | Michelson | 600/232 X |
| 5,503,617 A | | 4/1996 | Jako | 600/201 |
| 5,616,117 A | * | 4/1997 | Dinkler et al. | 600/232 |
| 5,893,831 A | * | 4/1999 | Koros et al. | 600/232 |
| 6,042,542 A | * | 3/2000 | Koros et al. | 600/232 X |

FOREIGN PATENT DOCUMENTS

| | | | | |
|---|---|---|---|---|
| DE | 618652 A | * | 9/1935 | .................. 600/227 |
| DE | 77 05 768 U1 | | 6/1977 | |
| DE | 3834358 C1 | * | 4/1990 | .................. 600/232 |
| DE | 91 00 113 U1 | | 5/1991 | |
| DE | 197 08 587 C1 | | 9/1998 | |
| FR | 2302078 A1 | * | 9/1976 | .................. 600/232 |

* cited by examiner

Primary Examiner—Jeffrey A. Smith
(74) Attorney, Agent, or Firm—Samuels, Gauthier & Stevens, LLP

(57) ABSTRACT

To reliably expose the treated organ during surgical procedures, retraction devices are used with a holding arm (2) to which clamps (1) or the like are fastened, so that the clamps (1) canquickly be replaced and brought into a new position at the holding arm (2), the holding arm (2) designed as a rod with a hollow space, in which a blade-shaped locking bar (13) is guided. The holding arm (2) has openings (3), and the locking bar (13) has notches (12) aligned with the openings (3), so that, in the unlocked position, the openings (3) are exposed, while, in the locked position they are partly covered by the locking bar (13). Clamps (1) with shafts (10) can be inserted into the openings (3). The shaft (10) of a clamp (1) has a groove (11), into which the locking bar (13) can be slid, so as to fasten the clamp (1) in the opening (1) of the holding arm (2). By moving the locking bar (13), all the clamps pertaining to a holding arm (2) can be fastened and loosened at the same time, and also can be brought into their specifically desired attitude. So that the clamps (1) at the holding arm (2) can be replaced quickly, a second inventive solution specifies that the holding arm (2) has openings (15) followed by a long hole (16) and a subsequent depression (17). A clamp (1) has at least one T-shaped head (14), which can be inserted into an opening (15), can be moved in the long hole (16) until it reaches the depression (17), and can be lowered into the depression (17). On the backside of the holding arm (2), a locking bar (18) can be inserted into a rail guide (19), so as to hold the T-shaped head or heads (14) fast in the depressions (17). The locking bar can have bores (20, 45) for accommodating further instruments or tools. A clamp preferably has two T-shaped heads (14).

18 Claims, 5 Drawing Sheets

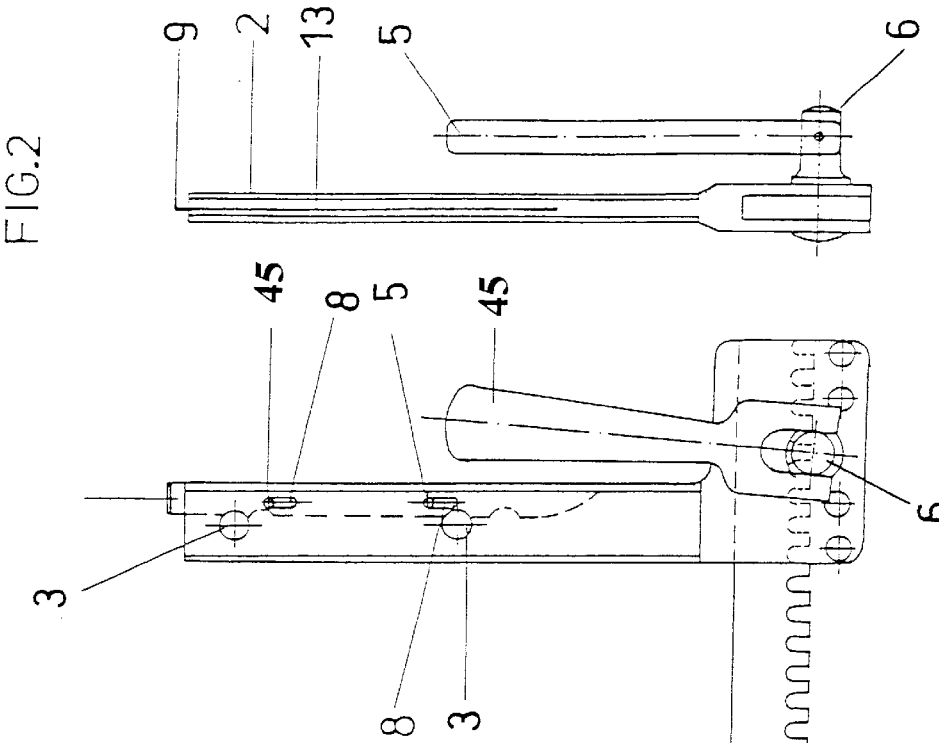
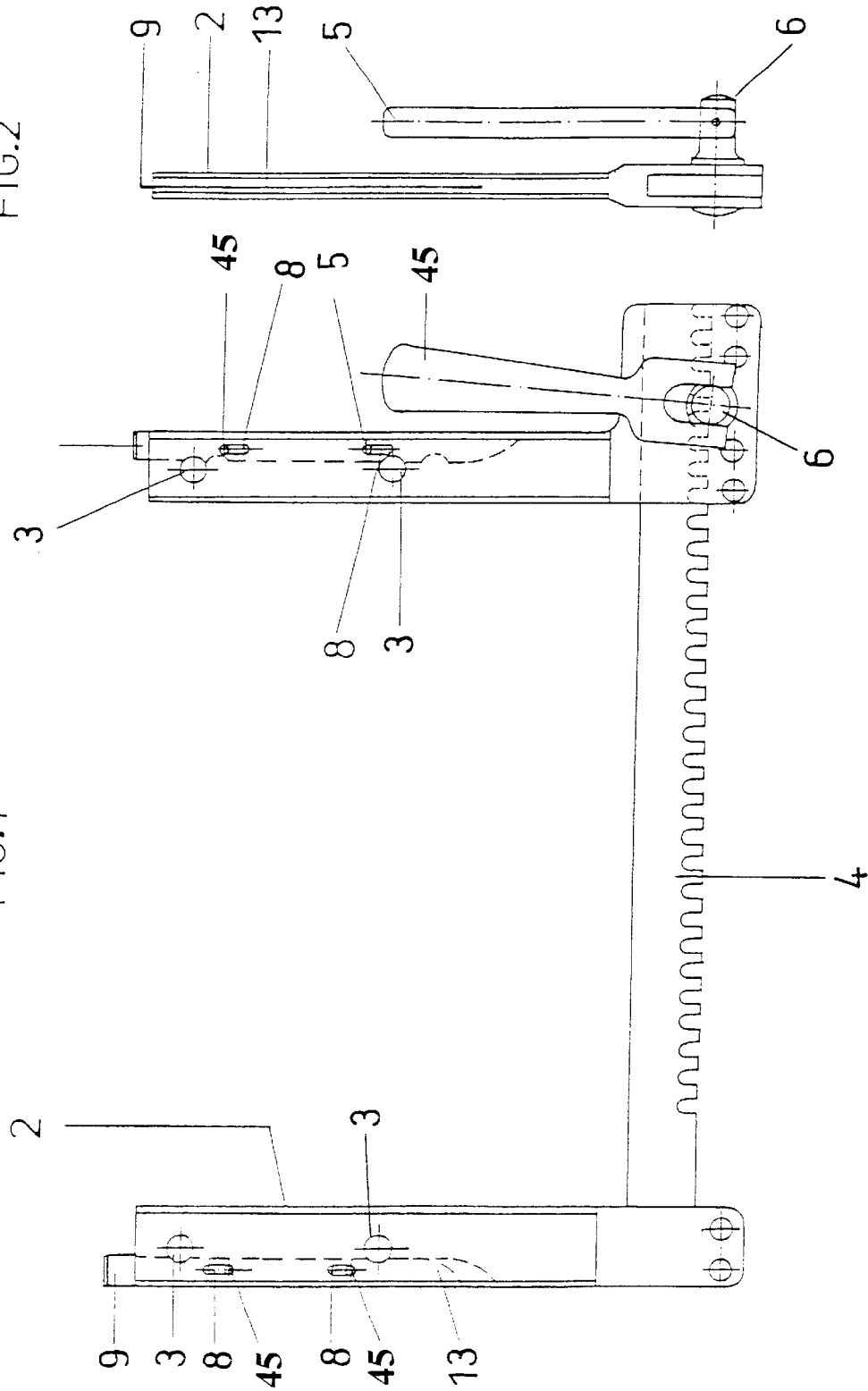

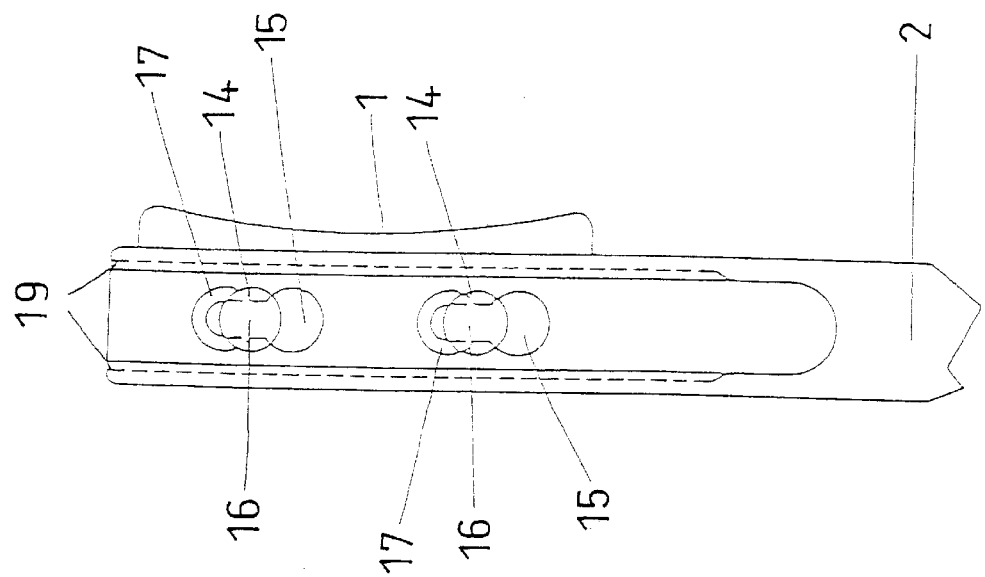
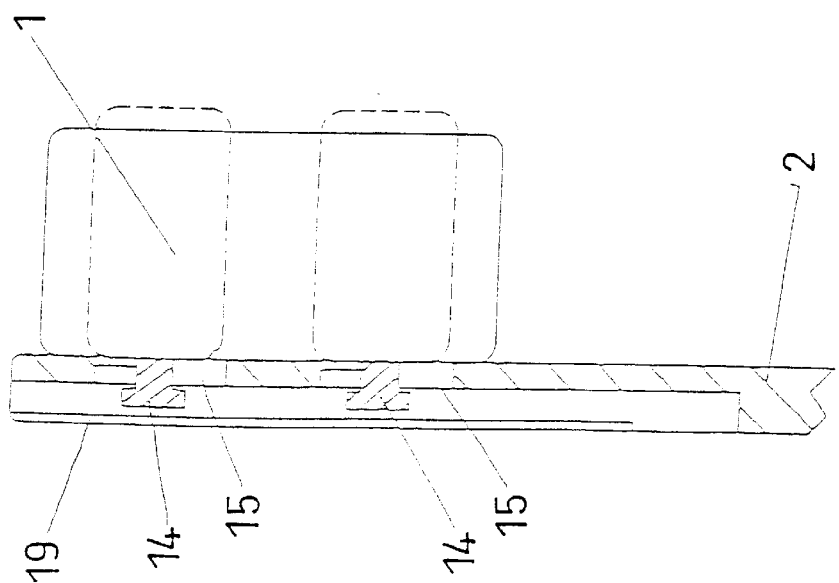

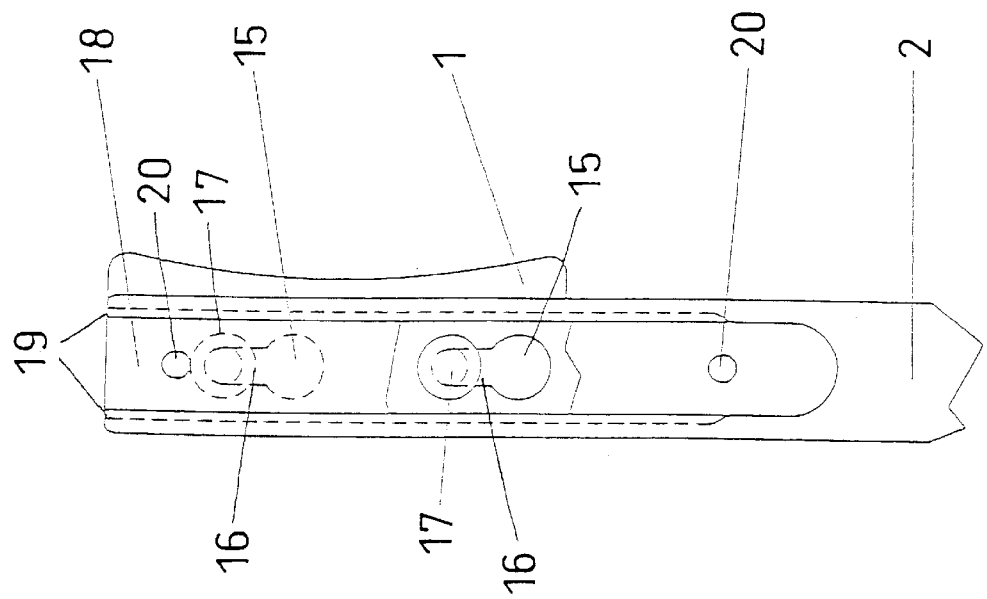
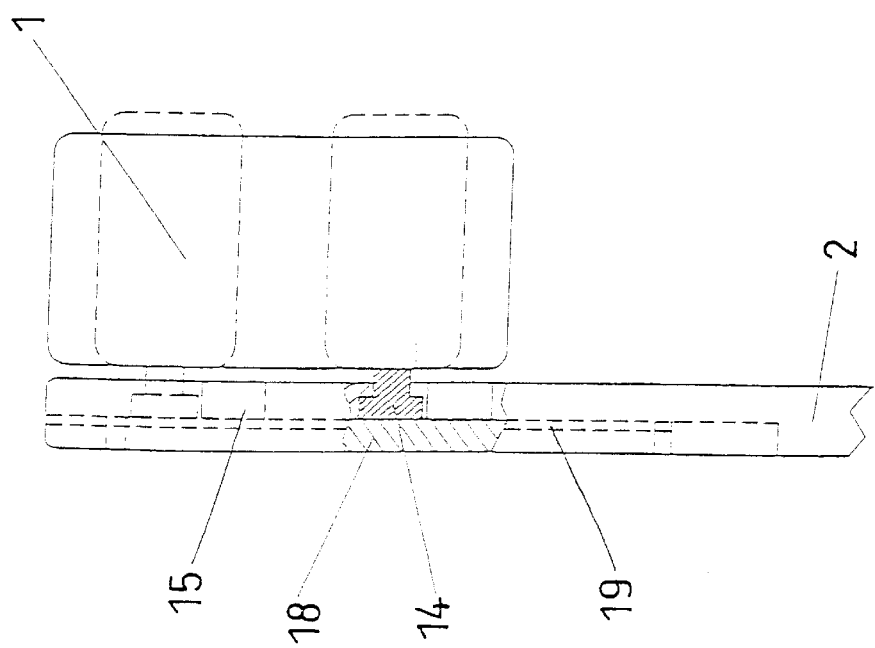

APPARATUS FOR RETRACTING TISSUE DURING SURGICAL PROCEDURES

BACKGROUND OF THE INVENTION

The invention relates to an apparatus for retracting tissue, tissue parts, organs, bones, or other body parts during surgical procedures on human or animal bodies, with a holder for fastening clamps (or the like), the holding arm having holes at prescribed intervals, and the clamps having a shaft that can be inserted into the holes of the holding arm.

In surgical procedures, the organ being treated is exposed by clamps at the edge of the surgical opening to hold fast the interfering tissue situated above the organ. These clamps are often also referred to as leaves and, depending on the application, are blade- or spoon-like plates or hooks. To perform different surgical procedures on different bodies, clamps of different form are always required, and these are fastened to the holder in the position and attitude that is best for the particular procedure.

U.S. Pat. No. 4,852,552 discloses a retraction device for retracting ribs and their surrounding tissue to expose the heart for a surgical procedure. As already described, the clamps are fastened to a holder, which is seated on a toothed rack and which can be fixed in several positions. A clamp is rotatably fastened to the holder by a screw connection, and is fixed in the desired position by another screw. Significantly, the retraction device requires that each clamp be fastened, locked in place, and loosened individually by a screw connection.

U.S. Pat. No. 5,503,617 describes a retractor endoscope for minimally invasive surgical procedures. An operating device is situated at one end of a rigid frame. A removable clamp is fastened at the other end to a rotatable clamp holding arm by a dovetail joint. A clamp holding arm is likewise rotatably fastened to a second frame, which can move relative to the rigid frame. A clamp is fastened to the holding arm by a dovetail joint. The two clamps can be adjusted independently of one another. At least one of the two clamps has a device for fastening fiber-optic light guides to illuminate the surgical opening.

German application DE 91 00 113.7 discloses a spreadable retractor at each of whose ends which are situated opposite the handle is fastened a replaceable clamp by a spring snap lock.

German application DE 77 05 768 U1 discloses a rapid action snap lock for clamps, to which one or more bearing pins with grooves are fastened. These are placed into receptacle holes provided for them in a frame, a rod, or a holding arm. When the bearing pin is inserted into the receptacle holes, a ball latches into the groove through the spring pressure created by a leaf spring or coil spring.

DE 197 08 587 C1 discloses a detachable holder for a blade—also referred to as a clamp—at the holding arm of a surgical retractor. A vertical slot and a slot slanted relative to the edge are machined into the holding arm. Two pins with a circumferential groove are disposed on the blade, and these can be inserted into the slots of the holding arm with a form-fit interlock. A blade is first inserted with a pin into the slanted slot, and is then turned about this pin, which acts as an axle, such that the other pin latches into the other slot. So the blade does not accidentally loosen from the holding arm, a flexible detent device is situated at the vertical slot of the holding arm. A ball is guided in a bore which leads laterally into the vertical slot of the holding arm, and this ball is pressed by a coil spring against the pin that is seated in the vertical slot. The other end of the bore is closed by a screw, against which the coil spring is supported. When the pin is swung into the slot with the detent device, the pin snaps into the slot behind the ball, and is pressed by the ball against the end of the slot. To remove the blade from the holding arm, the operator must overcome the force that the coil spring exerts on the pin.

A first disadvantage of this known holder is that the detent device, including of the bore, the ball, the coil spring, and the locking screw, requires a complicated and expensive manufacturing process.

A second disadvantage is that the detent device can become non-functional through contamination of the bore, the spring, and the ball.

A third disadvantage finally is that the detent device cannot be cleaned, unless the locking pin, the spring, and the ball are disassembled, cleaned individually, and then reinstalled, which takes some time.

SUMMARY OF THE INVENTION

An object of the invention to provide a retraction device that includes clamps that can be quickly and reliably fastened, loosened and replaced, and also fixed at various positions/attitudes.

In one embodiment, the holding arm is designed as a rod with a hollow space, within which a blade-shaped locking bar is guided. The locking bar has notches that have substantially the same spacing as the openings in the holding arm, and which expose the openings in the holding arm in the unlocked state, while, in the locked state, the notch-free areas of the locking bar partly cover the openings in the holding arm, and in that the locking bar can be pushed into a groove of the shaft, so as to fasten the clamps or the like on the holding arm.

In a second embodiment, a long hole whose width is less than the diameter of the opening, follows each opening whose end is followed by a depression, whose cross section is the same as the cross section of the opening, and in that the shaft of the clamp is designed as a T-shaped head, whose larger cross section corresponds to the cross section of the opening and the depression, and whose smaller cross section corresponds to the width of the long hole, so that the T-shaped head of a clamp can be inserted into the opening, can be moved in the long hole as far as the depression, and can be lowered into the depression, and in that a locking bar on the backside of the holding arm can be inserted into a rail guide so as to fix the T-shaped head in the depression.

To install, remove, or replace a clamp, the locking bar is brought into the unlocked position where its notches are aligned with the openings of the holding arm. In this state, the clamps can be removed from the holding arm and inserted in the holding arm by placing the shafts of the clamps into the holding arm. Furthermore, the clamps can be turned into the desired attitude. They are locked by moving the locking bar from the unlocking position into the locking position, so that the locking bar slides into the groove of each shaft of a clamp, and in this way fastens the clamp and at the same time locks it in place. The locking bar can be secured against opening, with a locking device (e.g., a screw connection).

Advantageously, the clamps can be fasted to the holding arm, locked in place, and again loosened at the same time by a small movement of the locking bar.

To fasten a clamp on a holding arm, with the second inventive solution, the T-shaped head of the clamp is placed into the opening. Then the head of the clamp is moved along the long hole, at the end of which it is pressed into the depression by pulling on the clamp. To lock it, a locking bar on the backside of the holding arm is placed into a rail guide. The locking bar holds the head of the clamp in the depression.

The opening, the depression, and the T-shaped head of the clamp preferably have a circular cross section. The diameter of the opening, the depression, and the large diameter of the T-shaped head of the clamp have the same size, while the smaller diameter of the head of the clamp corresponds to the width of the long hole.

The cross sections of the opening, the depression, and the head of the clamp need not be circular. For example, they can be triangular, rectangular, diamond-shaped, square, hexagonal, etc. They only need to have the same shape, so that the head of the clamp can be inserted into the opening with a positive form fit, can be moved in the long hole, and can be lowered into the depression.

One clamp may have for example two T-shaped heads. The rail guide for the locking bar, which presses the heads of the clamps into the depression, preferably includes a T-groove. The locking bar may have, for example, accommodations for surgical instruments, which are preferably bores. The clamps and the T-shaped heads may for example be made of one piece. Alternatively, the heads also can be welded to the clamps.

These and other objects, features and advantages of the present invention will become more apparent in light of the following detailed description of preferred embodiments thereof, as illustrated in the accompanying drawings.

BRIEF DESCRIPTION OF THE DRAWING

FIG. 1 illustrates two holding arms with a locking bar;

FIG. 2 illustrates a holding arm with a locking bar in a side view;

FIG. 8 illustrates a cross section through a holding arm with a clamp inserted, when the clamp is moved, through the long hole into the depression;

FIG. 9 illustrates a top view of the holding arm with the locking bar and the clamp, during the move through the long hole into the depression;

FIG. 10 illustrates a cross section through the holding arm with a locking bar and with a clamp fastened in its end position; and FIG. 11 illustrates a top view of the holding arm with the locking bar and with the clamp fastened in its end position.

DETAILED DESCRIPTION OF THE INVENTION

Figure 4:
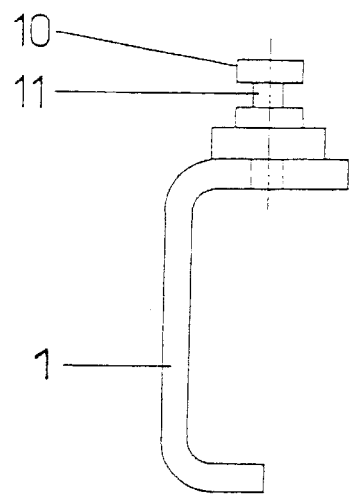
FIG. 4 illustrates a clamp.

FIG. 1 illustrates two holding arms 2 on a toothed rack 4, one of which is stationary while the other one can be moved and positioned along the toothed rack 4, for example, by a mechanism including a lever 5 and a drive 6.

The holding arm 2 includes a rod with a rectangular cross section and a hollow space into which a locking bar 13 is guided. The holding arm 2 has several (e.g., two) crosswise openings 3 that penetrate all the way through. The locking bar 13 has two notches 12 that are aligned with the openings 3 at the same distance. In the unlocked position the notches 12 are aligned with the openings 3 of the holding arm 2, so that the openings 3 of the holding arm 2 are free. In this unlocked state, the shafts of the clamps can be placed into the openings 3. To bring the locking bar into the locked position, it is moved in the hollow space of the holding arm 2, so that the notches 12 of the locking bar 13 are no longer aligned with the openings 3 of the holding arm 2. As a result, these openings 3 are partly covered by the locking bar 13. The holding arm 2 has two bores 45 that are aligned with two longitudinal holes 8 in the locking bar 13, and which are connected with one another by a screw connection. This screw connection serves as a stop and also to guide the locking bar 13 in the hollow space. It can also be used to secure the locking bar 13 in its locked position. A stop 9 is situated at that end of the locking bar 13 which extends from the holding arm 2. The locking bar 13 is slightly bent like a leaf spring, so that it is secured against sliding in the hollow space. The hollow space corresponds to the shape of the locking bar and it is preferably disposed in the center of the holding arm 2, so that the clamps can be affixed from both sides. This is highly advantageous in surgery.

FIG. 2 illustrates one of the holding arms 2 with a lever 5 of the detent device, also a locking bar 13 seated in the hollow space of the holding arm 2. The stop 9 is disposed at that end of the locking bar 13 that extends from the holding arm 2.

Figure 3:
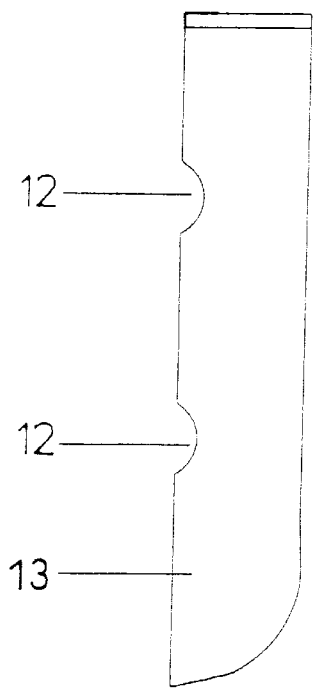
FIG. 3 is a side view illustration of a locking bar in a side view.

FIG. 3 is a side view illustration of the locking bar 13.

FIG. 4 illustrates a side view of the clamp 1 and the shaft 10. The shaft 10 has a groove 11 into which the locking bar 13 slides during the locking process. The shaft 10 and the clamp 1 can be made of one piece. However, the shaft 10 can for example also be welded to the clamp 1.

Referring to FIGS. 1, 3 and 4, the two notches 12 of the locking bar 13 are semicircular in shape, while the openings in the holding arm 2 are circular. Two longitudinal holes 8 are disposed in the locking bar 13. These are aligned with the bores 45 in the holding arm 2. A screw connection is inserted through them to guide the locking bar 13 in the holding arm 2. The openings 3 in the holding arm 2 and the shaft 10 of a clamp 1 can, for example, be circular, square or hexagonal. However, if the clamp 1 has a shape with edges it can no longer be turned in the opening 4.

Figure 5:
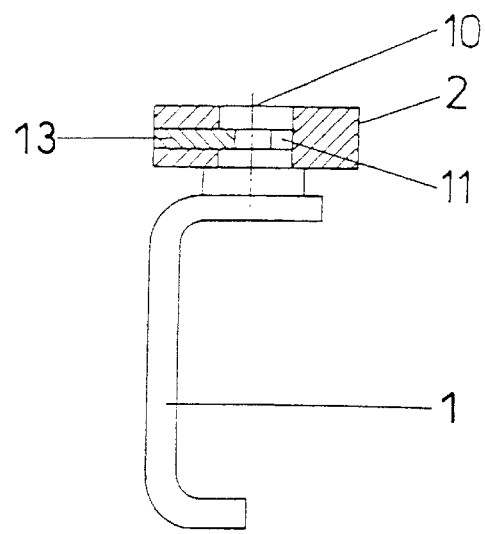
FIG. 5 illustrates a clamp in its locked state.

FIG. 5 illustrates the clamp in the locked position.

The shaft 10 and the clamp 1 are seated in an opening 3 of the holding arm 2. The locking bar 13 is pushed into the groove 11 of the shaft 10, and thus locks the clamp 1 in place at the holding arm 2. The clamp 1 now can neither be removed from the holding arm 2 nor turned in the opening 3 of the holding arm 2.

Figure 6:
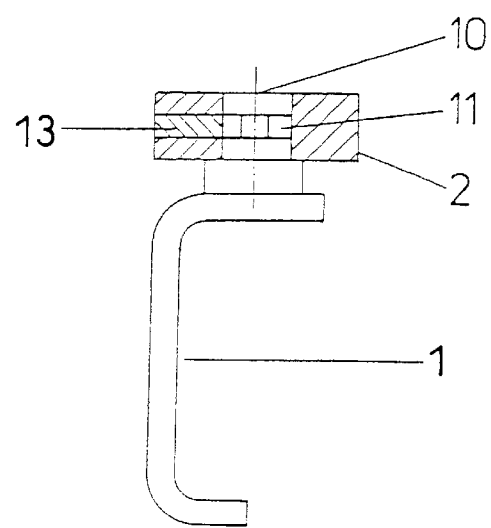
FIG. 6 illustrates the clamp in its unlocked state.

FIG. 6 illustrates the clamp 1 in its unlocked state.

Referring again to FIG. 5, the shaft 10 of the clamp 1 is seated in the opening 3 of the holding arm 2; however, the groove 11 of the shaft 10 now lies exposed, because the semicircular notch 12 of the locking bar 13 is aligned with the opening 3 of the holding arm 2. In this unlocked state, the clamp 1 can be turned in the opening 3 of the holding arm 2 or can be removed from the opening 3, for example to insert a clamp 1 with a different shape.

With the inventive retraction device, limited manipulation is needed to move the locking bar 13 from the locked position to the unlocked position and vice versa. In the unlocked position of the locking bar 13, the clamps 1 can be removed from the holding arm 2 and other clamps can be installed, and also can be turned into the desired attitude. By moving the locking bar into the locked position, all the clamps situated in the holding arm 2 are fastened and locked in place. The inventive retraction device can be equipped with other clamps very quickly and with little manipulation. Because all the clamps are fastened with only one locking bar 13, instead of having screw connection for each clamp, the inventive retraction device can be manufactured very economically. Of course, not only clamps but all possible surgical instruments and tools can be fastened at the holding arm 2 on both sides.

Figure 7:
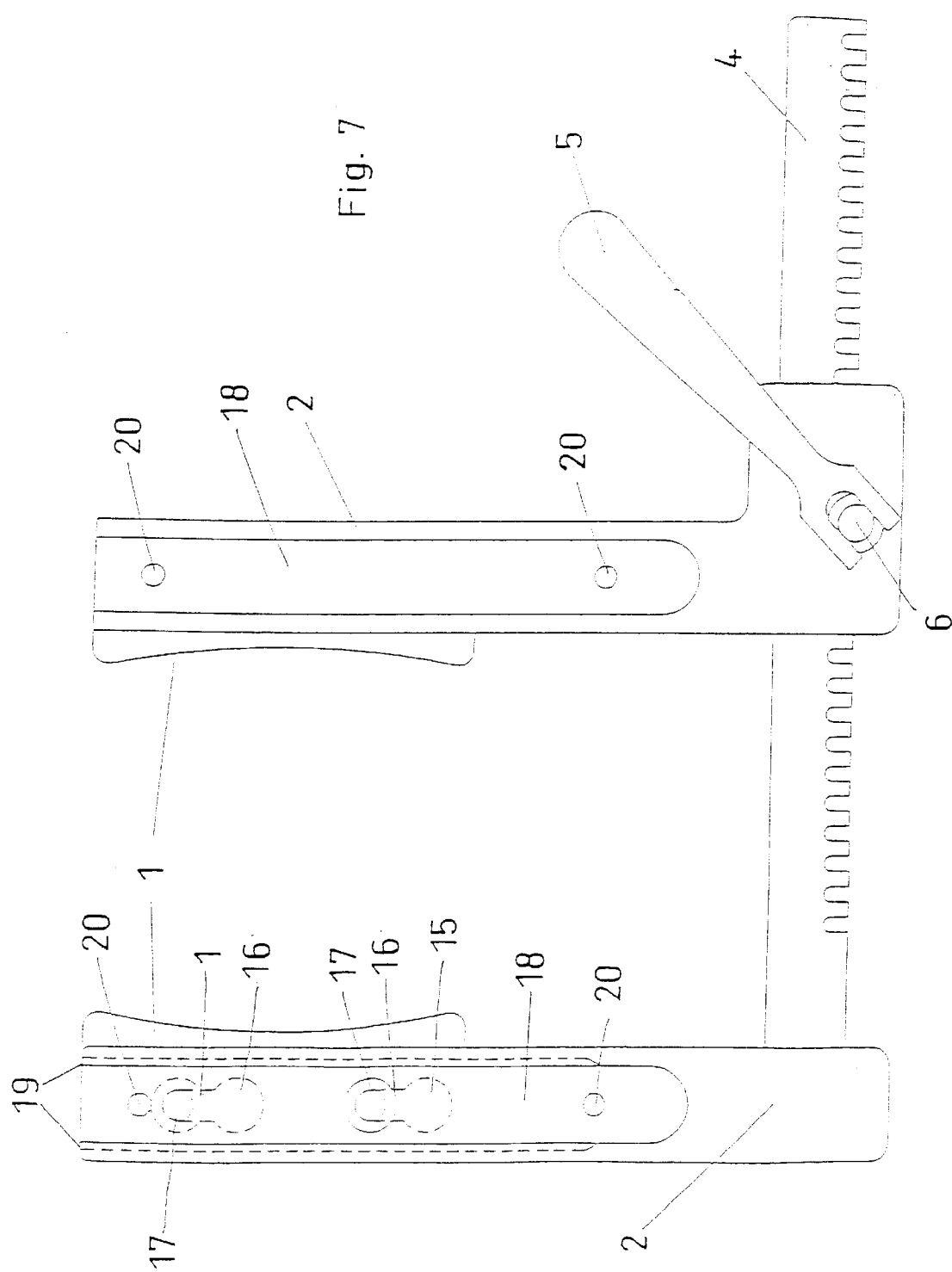
FIG. 7 is an alternative embodiment illustration of two holding arms with locking bars.

As illustrated in FIG. 7, the holding arms 2 are seated on the toothed rack 4. A first of the holding arms is stationary, while the second arm is arrested on the toothed rack 4 by a mechanism that includes the lever 5 and the drive 6. The second holding arm can be moved continuously to an arbitrary position. The two holding arms 2 have several (e.g., two), openings 15, long holes 16 and depressions 17. A locking bar 18 can be inserted into a rail guide 19 on the backside of the holding arm 2.

FIG. 8 illustrates a cross section through a holding arm 2, to which the clamp 1 will be fastened. The clamp 1 has two shafts 14 that each include as a T-shaped head. The two T-shaped heads 14 are situated in the long hole 16 of the holding arm 2, after they have been inserted through the opening 15. The rail guide 19 for the locking bar 18 is situated on the backside of the holding arm 2.

FIG. 9 shows the backside of the holding arm 2 with the two openings 15, the two long holes 16 and the two depressions 17. The two T-shaped heads 14 of the clamp 1 are situated in the two long holes 16. To fasten the clamp 1 on the holding arm 2, the clamp 1 is pushed further toward one end of the long hole 8, until the T-shaped heads 14 latch into the depressions 17. Then the locking bar 13 is inserted into the rail guide 19, to arrest the T-shaped heads 14 of the clamp 1 in the depressions 17.

FIG. 10 shows a cross section through the holding arm 2 with the clamp 1 fastened in its end position. The T-shaped heads 14 of the clamp 1 lie in the depressions 17, and are held by the locking bar 18, which is inserted in the rail guide 19.

FIG. 11 shows the backside of the holding arm 2 with the clamp 1 fastened in its end position.

The locking bar 18 has two accommodations, designed as bores 20, for fastening other surgical instruments or tools.

The inventive retraction device can be equipped with one or more clamps. For this, the locking bar is removed from its rail guide, the shafts of the clamps are placed into the insert openings and the clamps are pushed into their end position so that the T-shaped heads latch into the depressions of the holding arm. Finally, to hold the clamps fast, the locking bar must be inserted into the rail guide. The clamps can be replaced just as easily. Another advantage of the inventive retraction device is that it can be cleaned very easily. Despite these advantages, the inventive retraction device is easily manufactured. Of course, not only clamps, but all possible surgical instruments and tools can be fastened on the holding arm.

Although the present invention has been shown and described with respect to several preferred embodiments thereof, various changes, omissions and additions to the form and detail thereof, may be made therein, without departing from the spirit and scope of the invention.

What is claimed is:

1. An apparatus for retracting tissue during a surgical procedure, comprising:

a toothed rack having a distal end and a proximate end;

first and second substantially parallel holding arms both disposed substantially perpendicular to said toothed rack, wherein said first holding arm is fixedly attached to said toothed rack at said distal end, and said second holding arm is slidably attached to and moves along said toothed rack;

a first clamp having a first shaft;

a second clamp having a second shaft;

wherein at least one of said first and second holding arms is shaped as a hollow rod formed by parallel side walls that extend along a longitudinal axis, and said at least one of said first and second holding arms includes A) a plurality of openings in at least one of said sidewalls, each of said openings sized to accept either of said first and second shafts and to attach said associated clamp to said one of said first and second holding arms, wherein said first shaft is placed into a first of said plurality of openings and said second shaft is placed into a second of said plurality of openings; and B) a blade shaped locking arm that is configured and arranged to slide within said hollow rod between a first position and a second position, and includes a first notch and a second notch both on an exterior edge of said blade shaped locking arm, which secures both first shaft and said second shaft to said holding arm as said locking arm is moved into said second position.

2. The device of claim 1, wherein the hollow space is situated in the middle of the holding arm.

3. The device of claim 2, wherein the locking bar is bent slightly so that it is secured against sliding in the hollow space.

4. The device of claim 3, wherein the holding arm has a square profile.

5. The device of claim 4, wherein the openings in said at least one of said first and second holding arms have corners, and the notches in the locking bar likewise have corresponding corners.

6. The device of claim 1, wherein the openings in said at least one of said first and second holding arms are circular and the notches in the locking bar are semi-circular.

7. The device of claim 1, wherein the holding arm has at least one bore, and the locking bar has at least one long hole aligned with this bore, and in that the locking bar is guided in the holding arm by a screw connection situated in the bore and the long hole.

8. The device of claim 7, wherein the locking bar can be locked in place by the screw connection.

9. The device of claim 8, wherein the end of the locking bar that extends from the holding arm has a stop.

10. The device of claim 9, wherein an annular groove is situated in said shaft of first clamp, so that said first clamp can be fixed at an arbitrary rotational position in the holding arm by the locking bar.

11. The device of claim 10, wherein the first shaft is circular.

12. The device of claim 13, wherein said first clamp and said first shaft are made of one piece.

13. The device of claim 10, wherein in that the first shaft of said first clamp has corners.

14. The device of claim 13, wherein said first shaft is welded to the first clamp.

15. The apparatus for retracting tissue of claim 1, wherein when said locking arm is moved from said second position to said first position, said first and second shafts may be removed from said opening to remove said first and second clamps from said at least one of said first and second holding arms.

16. The apparatus for retracting tissue of claim 1, wherein as said blade shaped locking arm is moved into said second position, said first and second notches are no longer aligned with said associated opening and said blade locking arm secures said first and second clamps to said at least one of said first and second holding arms.

17. The apparatus for retracting tissue of claim 1, wherein said second holding arm comprises a lever that engages said toothed rack in a first lever position to prevent said second holding arm from sliding along said toothed rack, and in a second lever position said second holding arm is allowed to slide along said toothed rack.

18. The apparatus for retracting tissue of claim 1, wherein said first shaft is configured as a T-shaped head.

\* \* \* \* \*